US006463331B1

(12) United States Patent
Edwards

(10) Patent No.: US 6,463,331 B1
(45) Date of Patent: Oct. 8, 2002

(54) APPLICATION OF ENERGY AND SUBSTANCES IN THE TREATMENT OF URO-GENITAL DISORDERS

(75) Inventor: Stuart D. Edwards, Portola Valley, CA (US)

(73) Assignee: Novasys Medical, Inc., Newark, CA (US)

( * ) Notice: Subject to any disclaimer, the term of this patent is extended or adjusted under 35 U.S.C. 154(b) by 0 days.

(21) Appl. No.: 09/539,264

(22) Filed: Mar. 30, 2000

Related U.S. Application Data
(60) Provisional application No. 60/130,405, filed on Apr. 19, 1999.

(51) Int. Cl.⁷ .............................................. A61B 18/18
(52) U.S. Cl. ........................ 607/101; 607/102; 606/29
(58) Field of Search ............................ 607/96, 98, 99, 607/101, 102, 104, 105, 113, 115, 116; 606/41–50, 13, 14, 15, 27–29

(56) References Cited

U.S. PATENT DOCUMENTS

| | | | |
|---|---|---|---|
| 5,549,644 A | * 8/1996 | Lundquist et al. | 604/22 |
| 5,558,673 A | 9/1996 | Edwards et al. | 606/41 |
| 5,575,788 A | 11/1996 | Baker et al. | 606/41 |
| 5,588,960 A | 12/1996 | Edwards et al. | 604/20 |
| 5,630,794 A | 5/1997 | Lax et al. | 604/22 |
| 5,800,482 A | * 9/1998 | Pomeranz et al. | 607/101 |
| 5,800,484 A | * 9/1998 | Gough et al. | 606/41 |
| 5,873,877 A | * 2/1999 | McGaffigan et al. | 606/41 |
| 5,882,346 A | * 3/1999 | Pomeranz et al. | 604/500 |
| 6,056,747 A | * 5/2000 | Saadat et al. | 606/50 |
| 6,216,027 B1 | * 4/2001 | Willis et al. | 600/424 |

OTHER PUBLICATIONS
US 5,401,172, 3/1995, Perkins (withdrawn)*

* cited by examiner

*Primary Examiner*—Roy D. Gibson
(74) *Attorney, Agent, or Firm*—Fish & Neave; Nicola A. Pisano

(57) ABSTRACT

This invention provides a method and system for the curative treatment of female uro-genital disorders. One aspect of the invention is that it allows the gynecologist to coagulate the entire endometrium and upper layers of the myometrium in one short procedure that can be performed in a physician's office or other outpatient setting, using local or regional anesthesia. A second aspect of the invention is that it can be used to tighten the urethral sphincter and bladder outlet.

42 Claims, 13 Drawing Sheets

FROM FIG. 9A

910 — The retractable lock pin 431 is manipulated so as to release the spring-loaded pin detail 422 from the speculum. The blade 420 is withdrawn from the vagina. The speculum is closed and removed.

FIG. 9B

APPLICATION OF ENERGY AND SUBSTANCES IN THE TREATMENT OF URO-GENITAL DISORDERS

INCORPORATED DISCLOSURES

This application claims the priority of U.S. Provisional Application No. 60/130405, Express Mail Mailing number EJ651971575US, filed on Apr. 19, 1999.

This invention is submitted in the name of the following inventor:

| Inventor | Citizenship | Residence Address |
|---|---|---|
| Stuart D. Edwards | United States | 658 Westridge Drive Portola Valley, CA 94028 |

The assignee is Genesis Medical Technologies, a California corporation having an office in Sunnyvale, Calif.

BACKGROUND OF THE INVENTION

1. Field of the Invention

This invention relates to treating menorrhagia, female urinary incontinence and other related uro-genital conditions.

2. Related Art

Female uro-genital tract disorders include menorrhagia (excessive uterine bleeding) and urinary incontinence. Although both menorrhagia and urinary incontinence cause much embarrassment, they frequently remain untreated.

Causes of menorrhagia include disorders within the uterus itself such as fibroids, and (more rarely) endometrial cancer. When a specific cause cannot be identified, the condition is termed dysfunctional uterine bleeding.

Causes of female urinary incontinence include disturbances in the complex interplay of anatomic structures that control continence such as hypermobility or intrinsic sphincteric deficiency. Hypermobility is a lack of anatomic stability caused primarily by weak surrounding tissue; intrinsic sphincteric deficiency is the inability of the urinary sphincter muscles to function properly as a valve or otherwise.

The known art of treating female uro-genital disorders includes a variety of different treatments. Treatments for menorrhagia include drug therapy, dilation and curettage (D & C), hysterectomy, myomectomy and hysteroscopic resection of the endometrium. Treatments for female incontinence include both maintenance measures (for example, diapers, pharmaceutical remedies, foley catheters, behavioral therapy and vaginal pessaries) and surgical treatments.

A first drawback to treatment of female uro-genital disorders involves the risks associated with the known art of surgical treatment of menorrhagia. Surgical approaches to the treatment of menorrhagia can be highly invasive, ineffective or high-risk procedures. In addition to causing sterility, procedures such as hysterectomy have a high complication rate, lengthy recovery time and place the patient at increased risk for osteoporosis. Procedures such as dilation and curettage are fertility-sparing, but are ineffective for removal of submucosal fibroids. Techniques such as hysteroscopic resection of the endometrium with ablation devices such as the electrode loop, the rollerball and the laser are highly technical and have only been adopted by a small number of highly trained gynecological surgeons.

A second drawback to the known art of treating female uro-genital disorders involves risks and inefficacy of surgical treatments of female urinary incontinence. Many of these treatments aim to (1) elevate and ensure support of the urethrovesical junction or (2) provide additional support to the bladderneck and associated structures by introducing bulking agents, foreign bodies and other substances. Most surgical treatments suffer from many of the same problems as do treatments of menorrhagia. Surgical treatment is not generally appropriate for all types of incontinence; it is particularly inappropriate for urge or mixed incontinence. Lastly, the support provided by bulking agents, foreign bodies and other substances tends to be very short term; such agents degrade and get absorbed into surrounding tissues, requiring retreatment.

A third drawback to the known art of treating female uro-genital disorders involves the relative inefficacy of maintenance approaches to urinary incontinence. These treatments all aim to provide a technique to help the patient deal with the condition and minimize lifestyle problems associated with incontinence. While these treatments may allow a patient to achieve a short-term measure of control, they do not remedy the underlying defect.

Accordingly, it would be advantageous to provide a method and system for treatment of female uro-genital disorders that is curative, easy to learn, requires only local or regional anesthesia, does not induce side effects and is not subject to drawbacks of the known art. This advantage is achieved in embodiments of an invention in which radiofrequency (RF) energy is applied to uro-genital tissues so as to cause shrinkage and remodeling, reshaping, bulking and other treatment effects.

SUMMARY OF THE INVENTION

This invention provides a method and system for the curative treatment of female uro-genital disorders by application of radiofrequency (RF) energy to targeted tissues. Application of this energy is selectively applied so as to ablate, tighten, shrink or reshape the tissue and thereby correct an unwanted condition.

A first embodiment of the invention involves using a radiofrequency generator and disposable treatment unit to deliver radiofrequency energy to the interior of the uterus, enabling a gynecologist or other medical personnel to coagulate the entire endometrium and upper layers of the myometrium in one short procedure that can be performed in a physician's office or other outpatient setting using local or regional anesthesia.

A second embodiment of the invention involves using a radiofrequency generator and a disposable treatment unit bearing two to four relatively small needle electrodes. The electrodes are positioned in the middle third of the urethra and energy is applied, causing shrinkage of the circular external urethral sphincter muscle. The tiny sites of treated muscle resorb, remodel and shrink in the weeks that follow treatment, causing a circumferential tightening of the urethral sphincter muscle. This treatment is curative of stress urinary incontinence that is, at least in part, secondary to sphincter muscle deficiency.

A third embodiment of the invention also involves using a radiofrequency generator and a treatment unit bearing two to four relatively small U-shaped electrodes. This treatment unit includes an irrigation balloon that is immediately proximate to the U-shaped electrodes. As saline irrigation cools and protects the bladder muscosa, RF energy is delivered to the submucosal bladder outlet musculature and connective tissue. The tiny sites of treated muscle resorb, remodel and shrink in the weeks that follow treatment, causing a circumferential tightening of the bladder outlet and a subsequent improvement in urinary continence via both decreased bladder outlet mobility and increased proximal urethra filling pressures.

A fourth embodiment of the invention also involves using a radiofrequency generator. The difference between this embodiment and the other embodiments is that the RF energy is delivered to the anterior and posterior regions of the vaginal wall. This has the effect of tightening of vaginal walls so as to increase support of the bladder outlet, proximal and mid-urethra. Moreover, circumferential tightening of the vaginal wall may provide physical and psychological improvement in the area of sexual function.

DETAILED DESCRIPTION OF THE PREFERRED EMBODIMENT

In the following description, a preferred embodiment of the invention is described with regard to preferred process steps and data structures. Those skilled in the art would recognize, after perusal of this application, that embodiments of the invention can be implemented using circuitry or other structures adapted to particular process steps and data structures, and that implementation of the process steps and data structures described herein would not require undue experimentation or further invention.

System Elements

Figure 1:
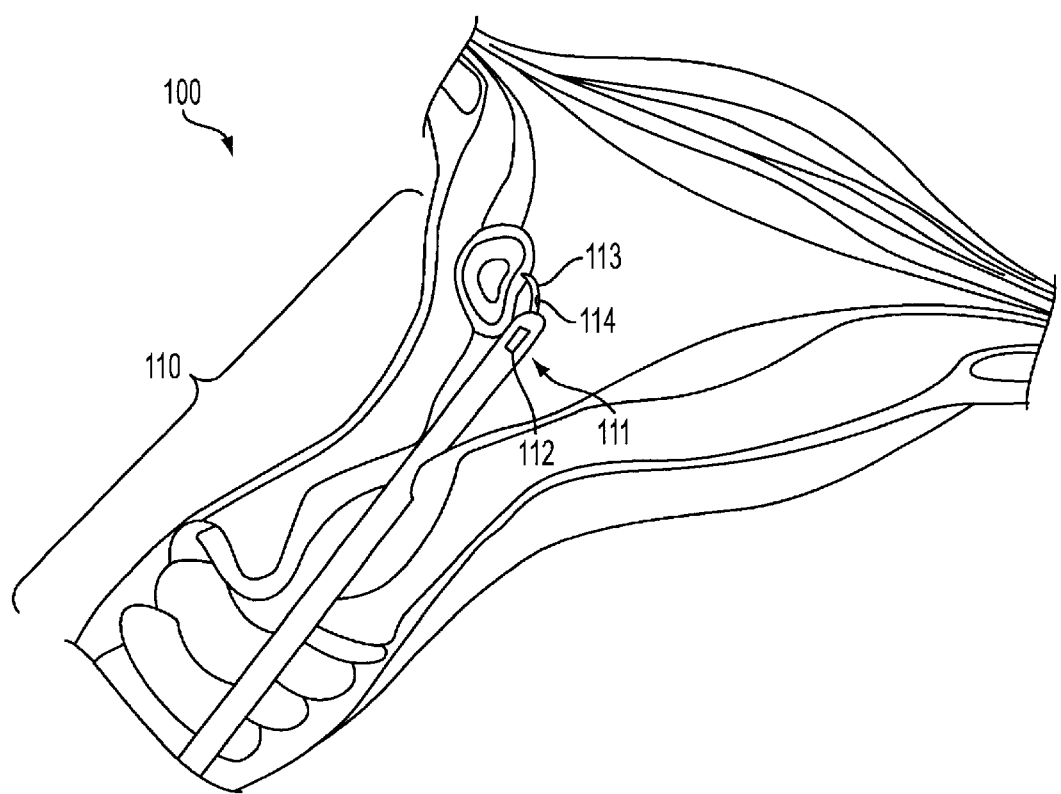
FIG. 1 is a block diagram showing a first embodiment of the distal end of a system that can be used for intrauterine ablation.

FIG. 1 is a block diagram showing a first embodiment of the distal end of a system that can be used for intrauterine ablation.

A system 100 includes a treatment element 110, a shaft and a control apparatus. The treatment element 110 is mounted on the most distal end of the shaft in such a way that the treatment element 110 and shaft form one contiguous piece. This figure is restricted to describing the treatment element 110. The shaft and control apparatus are described in greater detail in FIG. 5.

The treatment element 110 includes a distal tip 111, an irrigation port 112, one or more electrodes 113 and a plurality of lumens 115 (not shown).

The distal tip 111 is composed of a long, relatively narrow tubular element composed of relatively stiff, biologically non-reactive plastic that is disposed for insertion into a uterus via the vagina and cervix. In a preferred embodiment, the distal tip 111 is an extension of the shaft 510 (described supra).

The irrigation port 112 is located at the most distal end of the distal tip 111. A variety of liquids can be administered through the irrigation port 112, including cooling liquids such as saline, Ringers or water, and pharmacological agents such as antibiotics, anti-inflammatories, anti-spasmodics and anesthetics.

In a preferred embodiment, suction can also be applied via the irrigation port 112 so as to remove fluids or to cause the interior of the uterus to be more closely conformed to the treatment element 110.

The electrodes 113 include needle-like tips mounted either at the very end of the distal tip 111 or placed equidistantly from each other around the exterior diameter of the distal tip 111. Each electrode 113 also includes a thermocouple 114 so that the temperature of each electrode 113 can be monitored separately.

In a preferred embodiment, the electrodes 113 are disposed to deliver RF 2 energy to the interior of a uterus. In other embodiments, the electrodes 113 may be disposed to deliver microwave, laser, ELF (extremely low frequency) or other therapeutic energies.

The lumens 115 are disposed to control the electrodes 113, transmit the RF energy or channel the fluids to the irrigation port 112. All of the lumens 115 traverse the entire length of the shaft. They terminate at the treatment element 110 either at an electrode 113, a thermocouple 114 or the irrigation port 112.

Figure 2:
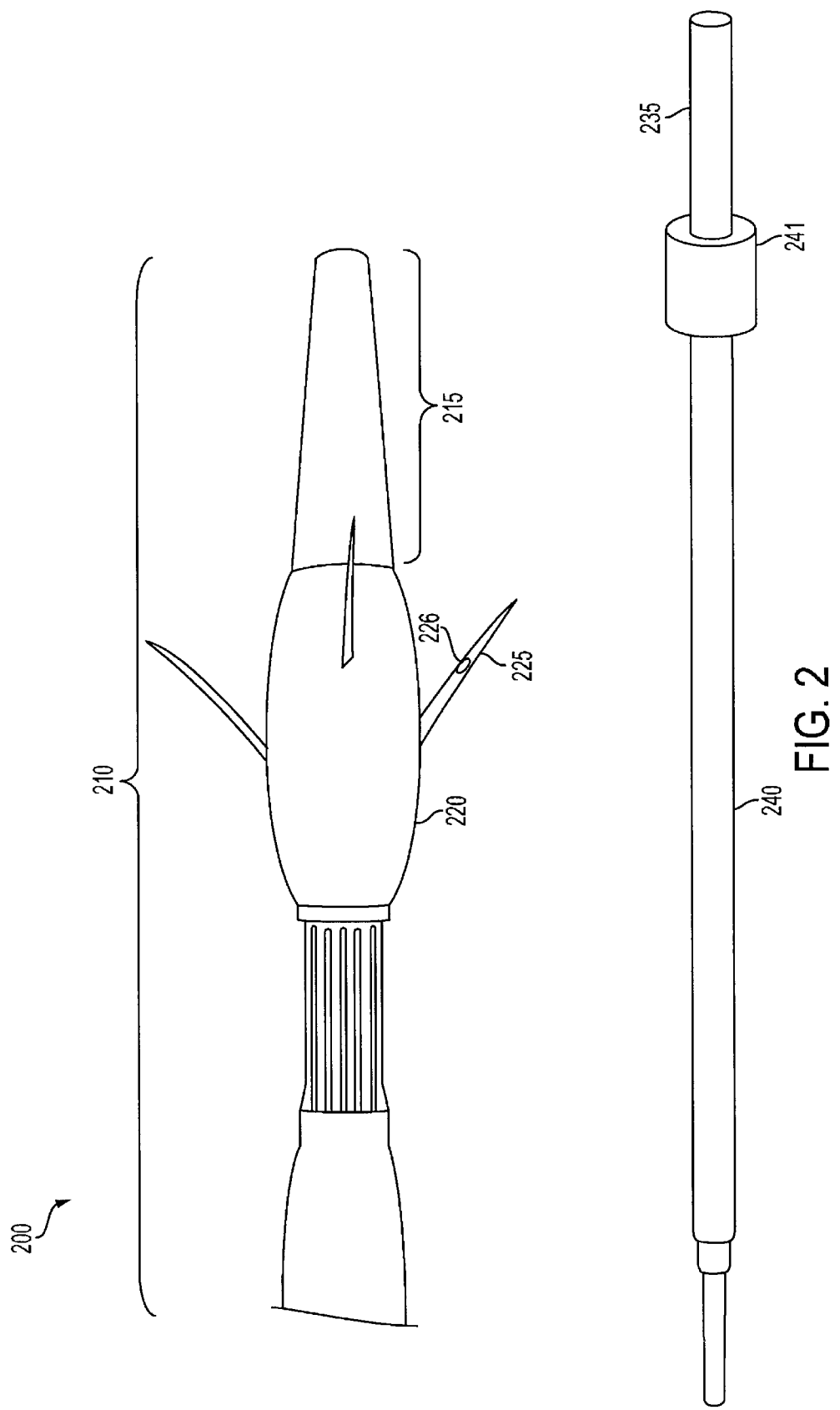
FIG. 2 is a block diagram showing a second embodiment of the distal end of a system that can be used for urethral remodeling.

FIG. 2 is a block diagram showing a second embodiment of the distal end of a system that can be used for urethral remodeling.

A system 200 includes a treatment element 210, a shaft and a control apparatus. The treatment element 210 is mounted on the most distal end of the shaft in such a way that the treatment element 210 and shaft form one contiguous unit. This figure is restricted to describing the treatment element 210. The shaft and control apparatus are described in greater detail in FIG. 5.

The treatment element 210 includes a distal tip 215, a sponge 220, a set of electrodes 225 and a plurality of lumens 230 (not shown) Depending upon the judgment of the physician, the treatment element 310 can be used in conjunction with the introducer 235 and sheath 240.

The distal tip 215 is mounted on the distal terminus of the shaft and control assembly (described supra). In a preferred embodiment, the distal tip 215 is composed of relatively stiff, biologically inert material that is disposed so as to be inserted into a urethra.

The sponge 220 is mounted on the proximal end of the distal tip 215. Although the relative length of the sponge 220 is comparable to the length of the distal tip 215, the non-compressed total diameter of the sponge 220 is approximately twice the diameter of the distal tip 215. In a preferred embodiment, the sponge 220 is disposed to be filled with saline or other cooling liquids that are delivered to the sponge 220 through one or more of the lumens 230. This cooling fluid serves to minimize thermal damage to tissues when the electrodes 225 are deployed. Delivery of other fluids, such as drug solutions may also be achieved using the sponge 220.

The electrodes 225 are take the form of very slightly arced needles that are approximately three fourths the total length of the distal tip 215. The electrodes 225 are positioned so they emerge from the middle section of the sponge 220 with each electrode 225 being relatively equidistant to the others around the exterior diameter of the sponge 220. The electrodes 225 emerge from the sponge at a 45 degree angle thereto, with the distal end of the electrodes 225 pointed in the general direction of the distal tip 215. The proximal end of each electrode 225 is coupled to a lumen 230 that is disposed to conduct radiofrequency or other types of energy to the electrode 225. The distal end of each electrode 225 is somewhat beveled so as to facilitate piercing the tissue. In a preferred embodiment, the system 200 includes four such electrodes; however, a greater or lesser number of electrodes are also possible.

Each electrode 225 includes at least one thermocouple 226. The thermo-couple 226 continuously measures the temperatures of each individual electrode 115. This constant temperature monitoring, combined with a computerized control algorithm allows each electrode 225 to be monitored separately in order to achieve safe and effective treatment temperatures. Any electrode 225 exceeding temperature safety limits can be immediately disengaged without aborting the entire procedure.

The plurality of lumens 230 traverse the entire length of the catheter from the control apparatus to the treatment element 210. Some of these lumens 230 can be disposed to deliver a variety of drugs, such as antibiotics, anesthetics and other pharmaceutical agents as deemed appropriate by the physician. Other lumens 230 are disposed to deliver cooling fluids such as saline, Ringers, sterile water or other solutions deemed appropriate by the physician. Still other lumens 230 are disposed to deliver energy to the electrodes 225. In a preferred embodiment, radiofrequency energy is used; however the lumens 230 of other embodiments may be used to deliver microwave, ultrasound, extremely low frequency (ELF), electromagnetic, laser and other forms of therapeutic energy.

The introducer 235 can be used in conjunction with the treatment element 210 and sheath 240. Use of the introducer 235 and sheath 240 is entirely optional. The introducer 235 a relatively long hollow tube made from a disposable, biologically nonreactive material. The overall diameter of the introducer 225 is such that it can be easily passed into a urethra. The interior diameter is such that the sheath 240 and treatment element 210 may be disposed to fit snugly inside the introducer 235.

The sheath 240 is a tube which is deployed inside the introducer 235. A hemoseal 241 forms within the sheath 240, thereby preventing the passage of urine, pus, cooling fluids or other substances out through the sheath 240.

In a preferred embodiment, the introducer 235 and sheath 240 are passed into the urethra as a single unit (that is, with the sheath 240 contained inside the introducer 235) through the urethra. The introducer 235 is removed, leaving the sheath 240 in place. The treatment unit 210 is inserted into and through the sheath 240, which is then pulled back several centimeters into the proximal urethra so that the treatment element 210 may be deployed. Following treatment, the treatment element 210 is drawn into the sheath 240 and removed from the urethra.

Figure 3:
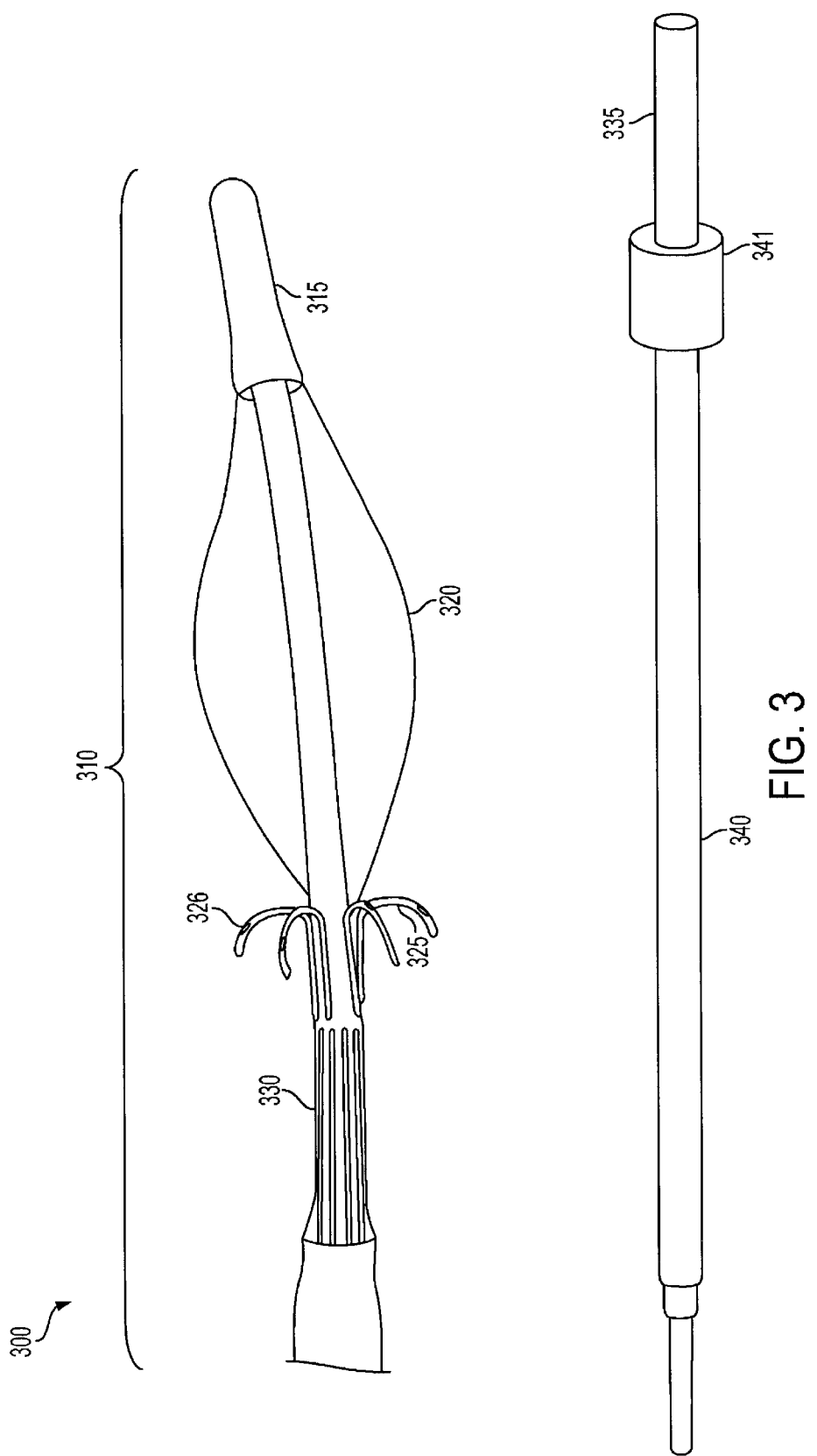
FIG. 3 is a block diagram showing a third embodiment of the distal end of a system that can be used for remodeling the bladder outlet.

FIG. 3 is a block diagram showing a third embodiment of the distal end of a device that can be used for remodeling of the bladder outlet.

A system 300 includes a treatment element 310, a shaft and a control apparatus. Similar to systems 100 and 200, the treatment element 310 is mounted on the most distal end of the shaft in such a manner that the shaft and treatment element 310 form one contiguous unit. This figure is restricted to describing the treatment element 310. The shaft and control apparatus are described in greater detail in FIG. 5.

The treatment element 310 includes a distal tip 315, an irrigation balloon 320, a set of U-shaped electrodes 325 and a plurality of lumens 330. The treatment element 310 is used in conjunction with the introducer 335 and sheath 340.

The distal tip 315 is mounted on the distal terminus of the catheter and control assembly (described supra). In a preferred embodiment, the distal tip 310 is composed of relatively stiff, biologically inert material that is disposed so as to be inserted into a urethra.

The irrigation balloon 320 is composed of microporous, transparent, biologically inert material. The distal end of the irrigation balloon 320 is fused with the proximal end of the distal tip 315; the proximal end of the irrigation balloon 320 is fused with the body of the shaft, immediately adjacent to the distal end of the U-shaped electrodes 325. The over length of the balloon 320 is approximately three times as long as the distal tip 315; the inflated diameter is approximately one and a half time the total length of the distal tip 315. In a preferred embodiment, the irrigation balloon 320 is disposed to provide a cooling surface and deliver cooling liquids to the bladder outlet and adjacent tissues.

Other preferred embodiments of the irrigation balloon 320 also include an external mapping electrode network 321 (not shown) that aids in the identification of nervous pathways responsible for the "urge sensation" and the involuntary detrussor muscle contractions that define urge urinary incontinence. Once identified, these pathways can be subsequently modified using nerve ablation techniques.

The set of U-shaped electrodes 325 are mounted on the shaft almost immediately proximate to the irrigation balloon 320. The proximal end of each U-shaped electrode 320 is coupled to a lumen 325; the distal end each U-shaped electrode 320 terminates in a beveled tip, with the beveled side facing away from the shaft in such a way that the hooked end can be easily deployed in the tissue of a bladder outlet. In a preferred embodiment, two—four U-shaped electrodes 325 are used. Other embodiments may deploy different arrays and different numbers of electrodes 325.

Each U-shaped electrode 325 includes at least one thermocouple 326. The thermocouple 326 continuously measures the temperatures of each individual electrode 325. This constant temperature monitoring, combined with a computerized control algorithm allows each U-shaped electrode 325 to be monitored separately in order to achieve safe and effective treatment temperatures. Any U-shaped electrode 325 exceeding temperature safety limits can be immediately disengaged without aborting the entire procedure.

The plurality of lumens 330 traverse the entire length of the shaft and terminate at the treatment element 310. Some of these lumens 330 can be disposed to deliver a variety of drugs, such as antibiotics, anesthetics and other pharmaceutical agents as deemed appropriate by the physician. Other lumens 330 are disposed to deliver cool fluids such as saline, Ringers, sterile water or other solutions deemed appropriate by the physician. Still other lumens 330 are disposed to deliver energy to the electrodes 325. In a preferred embodiment, radiofrequency energy is used; however, in other embodiments, the lumens 330 may be used to deliver microwave, ultrasound, extremely low frequency (ELF), electromagnetic, laser and other forms of therapeutic energy.

The introducer 335 is used in conjunction with the treatment element 310 and sheath 340. The indroducer 335 a relatively long hollow tube made from a disposable, biologically nonreactive material. The overall diameter of the introducer 225 is such that it can be easily passed into a bladder. The interior diameter is such that the sheath 340 and treatment element may be disposed to fit snugly inside the introducer 335.

The sheath 340 is a tube which is deployed inside the introducer 335. A hemoseal forms within the sheath 340, thereby preventing the passage of urine, pus, cooling fluids or other substances out through the sheath 340.

In a preferred embodiment, the introducer 335 and sheath 340 are passed into the bladder as a single unit (that is, with the sheath 330 contained inside the introducer 335) through the urethra. The introducer 335 is removed, leaving the sheath 340 in place. The treatment unit 310 and catheter are inserted into and through the sheath 340, which is then pulled back several centimeters into the proximal urethra so that the treatment element 310 may be deployed. Following treatment, the treatment element 310 is drawn into the sheath 340 and removed from the urethra.

Figure 4:
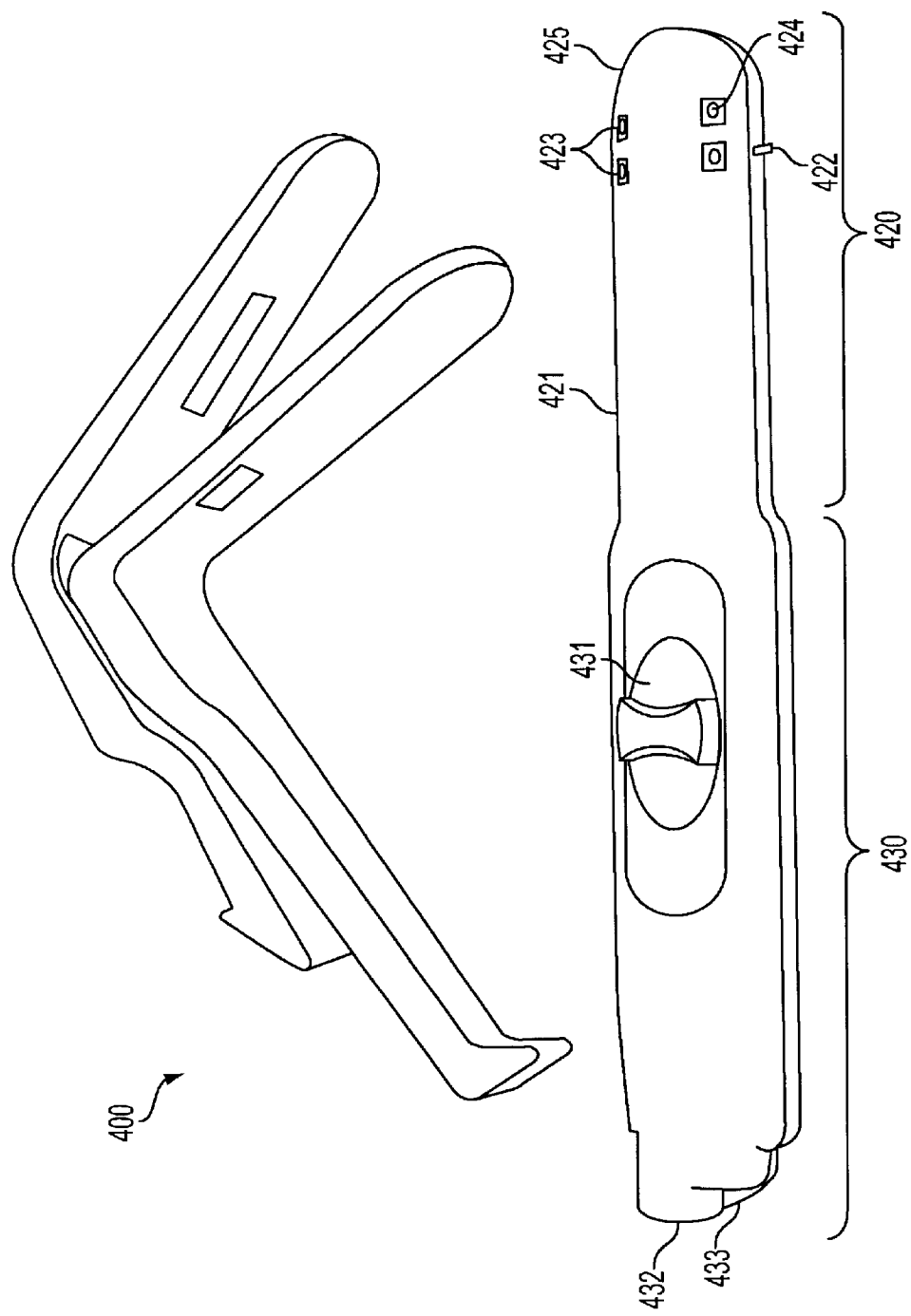
FIG. 4 is a block diagram showing a fourth embodiment of the distal end of a system that can be used for vaginal remodeling.

FIG. 4 is a block diagram showing a fourth embodiment of a device that can be used for vaginal remodeling.

A system 400 includes a treatment element 410. The proximal end of the treatment element 410 is coupled to an RF generator. The distal end of the treatment element 410 is inserted into a vagina using a speculum.

The treatment element 410 includes a blade 420 and a handle 430 composed of relatively hard, biologically non-reactive plastic. In a preferred embodiment the blade 420 and handle 430 form a single contiguous unit. A plurality of lumens 440 (not shown) traverse the interior length of the blade 420 and handle 430.

The blade 420 includes mating features 421, a spring-loaded pin detail 422, a plurality of relatively flat electrodes 423 and a plurality of irrigating fluid delivery pores 425.

The mating features 421 are constructed to engage with features in the speculum following simple positioning of the speculum within the vagina.

The spring loaded pin detail 422 locks the blade 420 into the correct position in the inserted speculum.

The plurality relatively flat electrodes 423 are each coupled to one or more of a series of lumens 440 that traverse the entire interior of the treatment unit 410 and terminate at the energy port 432 on the handle 430. In a preferred embodiment, these electrodes 423 are disposed to deliver RF energy. However, in other embodiments the electrodes 423 may also deliver microwave energy, ELF (extremely low frequency energy), laser and other forms of therapeutic energy.

Each electrode 423 includes at least one thermocouple 424 that is used to monitor the temperature of each electrode 423. This constant temperature monitoring, combined with a computerized control algorithm, is utilized to independently control the electrodes 423. If one of the electrodes 423 exceeds temperature safety limits, that particular one of the electrodes 423 can be disengaged without aborting the entire procedure.

The irrigating fluid delivery pores 425 are also coupled to some of the plurality of lumens 440 and are disposed to deliver cooling liquids so as to minimize thermal damage.

The handle 430 includes a retractable lock pin 43 1, an energy port 432 and two irrigating fluid ports 433.

The retractable lock pin 431 controls the spring-loaded pin detail 422 so that when the retractable lock pin 431 is engaged, it causes spring-loaded pin detail 422 to become locked into position in the speculum.

The energy port 432 is located at the proximal end of the handle 430 and is disposed to be coupled to an RF generator or other energy source. The energy port 432 is coupled to the proximal end of the plurality of lumens 440 that run through the interior of the handle 430 and blade 420 terminating a t the electrodes or cooling liquid ports 425.

The irrigating fluid delivery port 433 is disposed to deliver irrigating fluids, drugs and other liquids such as may be deemed appropriate. The fluids are introduced through one of the irrigating fluid delivery port 433 through the lumens 440 to the irrigating fluid delivery pores 425. The fluids are removed from the body through the other irrigating fluid delivery port 433.

Figure 5:
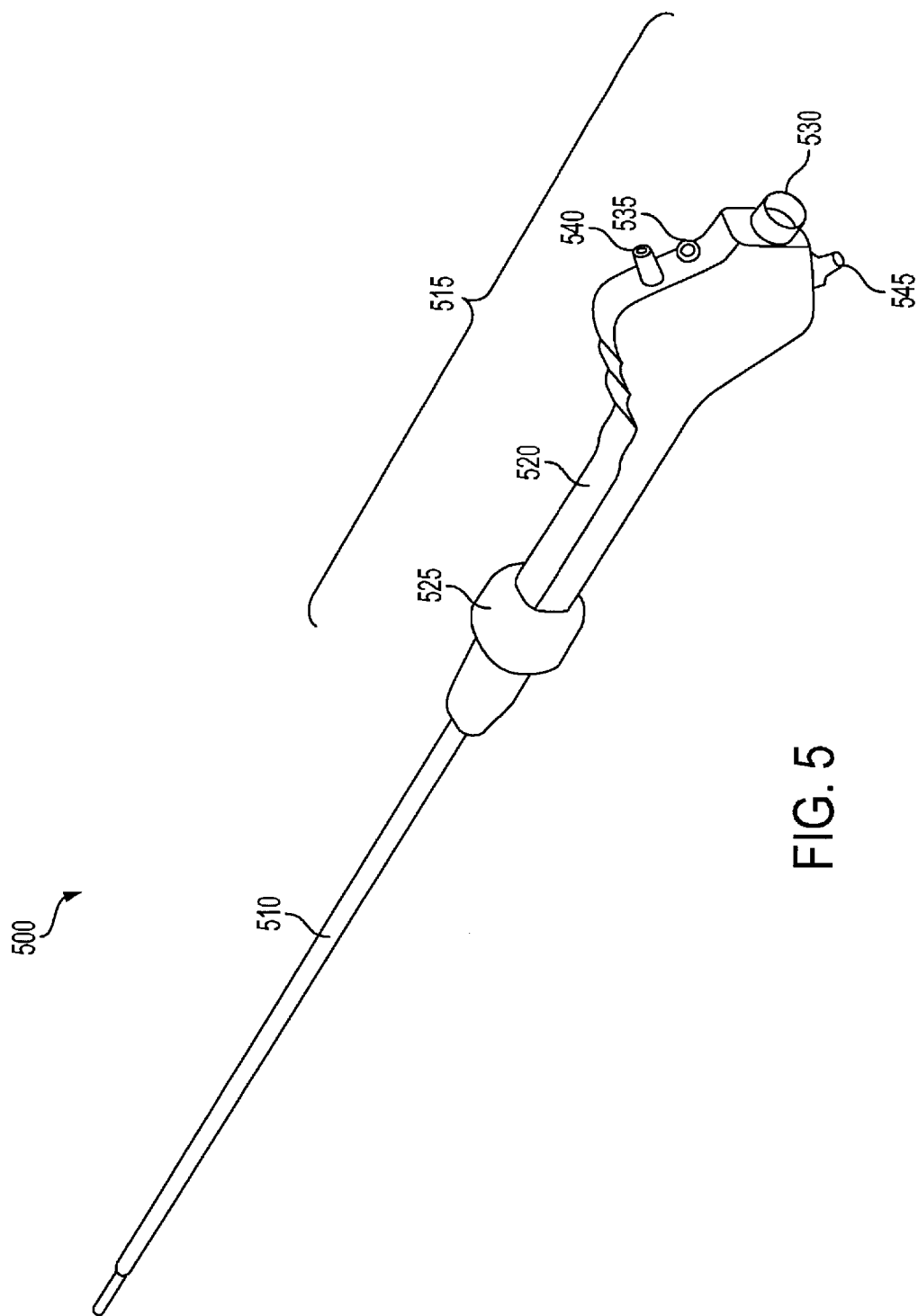
FIG. 5 is a block diagram showing the proximal end of systems for intrauterine ablation, urethral remodeling and bladder outlet remodeling.

FIG. 5 is a block diagram showing the proximal end of devices for intrauterine ablation, urethral remodeling and, bladder outlet remodeling.

A system 500 is used to control the delivery of energy and fluids through the first, second and third embodiments described infra (that is devices for intrauterine ablation, urethral remodeling and, bladder outlet remodelling).

A system 500 includes a shaft 510 and control apparatus 515. The control apparatus 515 houses all the elements needed to control the treatment element 110, treatment element 210 or treatment element 310. As such, the control apparatus 515 includes a handle 520, a electrode control element 525, an electric connector 530, a fluid input port 535, a fluid output port 540 and an inflation control port 545.

The shaft 510 is a relatively long tubular element, coupled on the distal end to treatment element 110, treatment element 210 or treatment element 310, and coupled on the proximal end to the control apparatus 515. The shaft 510 is comprised of relatively hard plastic and is disposed to house lumens 130, lumens 230 or lumens 340, which traverse the entire length of the shaft 510.

The electrode control element 525 is mounted on the most distal portion of the control apparatus 525 immediately adjacent and contiguous with the handle 520. The electrode control element 525 is coupled to proximal end of some of the lumens 130, lumens 230 or lumens 340. As such, the electrode control element 525 can be used to activate or deactivate electrodes includes in systems 100, 200 or 300. These electrodes can be controlled either individually or in combination.

The electric connector 530 is mounted on the most proximal end of the control apparatus 525. As such, it is coupled to the most proximal end of some of the lumens 130, 230 or 330 that traverse the interior of the shaft 510 and handle 520. In a preferred embodiment, the electric connector 530 is disposed to be connected to an RF generator. In other embodiments, the electric connector 530 can be disposed to be connected to a generator of microwaves, ELF, laser or other therapeutic energy.

The fluid input port 535 is mounted immediately between the electric connector 530 and the fluid output port 540 on the top portion of the control apparatus 525. The proximal end of some of the lumens 130, lumens 230 or lumens 340 terminate at the fluid input port 525.

In a preferred embodiment, the fluid input port 525 is disposed to be coupled to a source of irrigating fluid, cooling liquids or pharmaceutical liquids. Substances that can be introduced through the fluid input port 525 include sterile saline, sterile water, Ringers, antibiotic solutions, local or regional anesthetics and other agents.

Fluid output port 540 is immediately adjacent to the fluid input port 535. The interior portion of the fluid output port 540 is coupled to some of the lumens 130, 230 or 330.

In a preferred embodiment the fluid output port 530 may be coupled to a pump or other apparatus to remove fluids.

The inflation control port 545 is used with the system 300 for remodelling the bladder outlet. The inflation control port 545 is situated adjacent to the electric connector 530 on the bottom side of the control apparatus 525. The interior of the inflation control port 525 is coupled to some of the lumens 330 that terminate in the irrigation balloon 320. Positive or negative pressure may be applied to the inflation control port 525 so as to inflate or deflate the irrigation balloon 320.

Method of Use

Figure 6A:
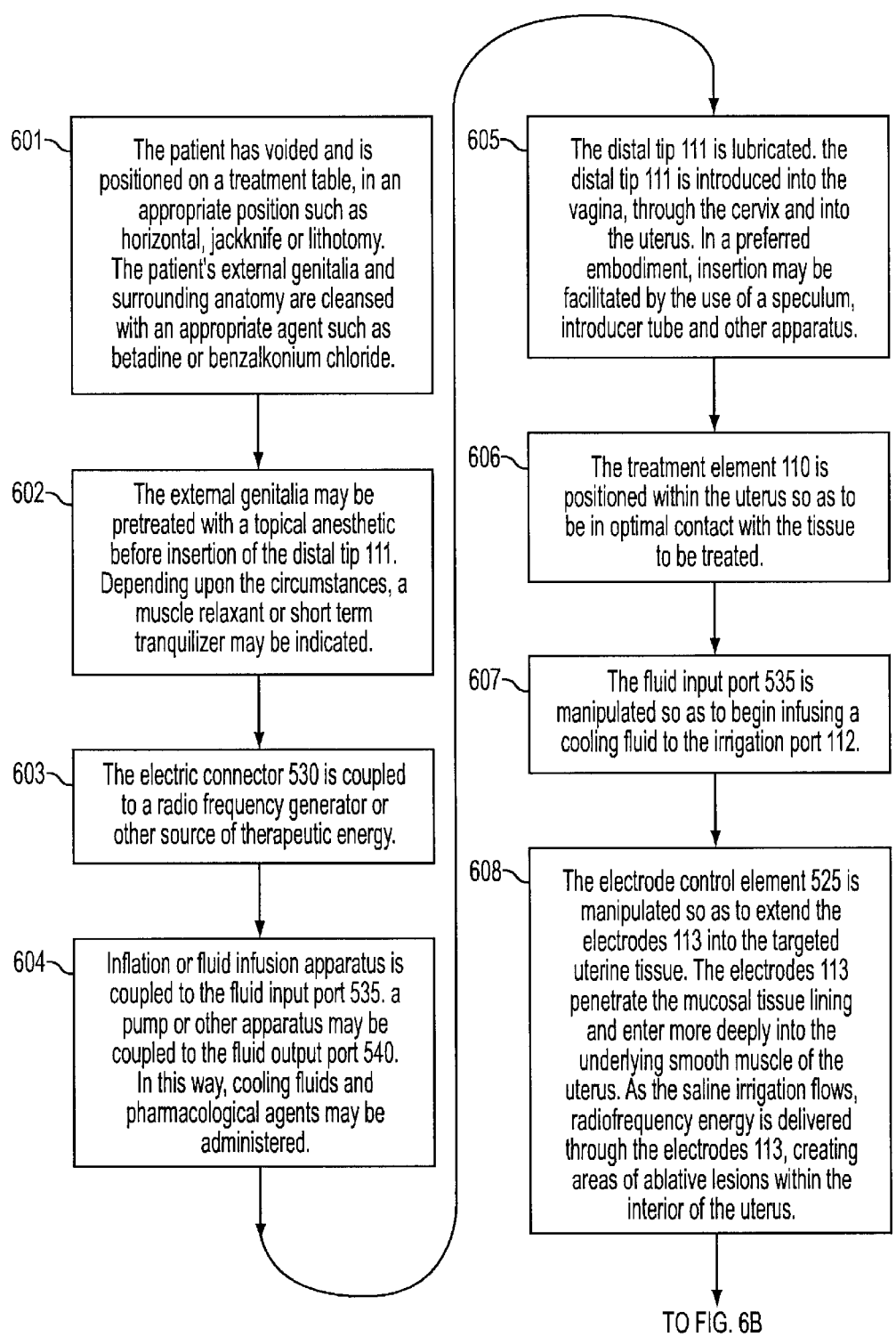
FIG. 6 is a process flow diagram showing method for using a first embodiment for intrauterine ablation.
Figure 6B:
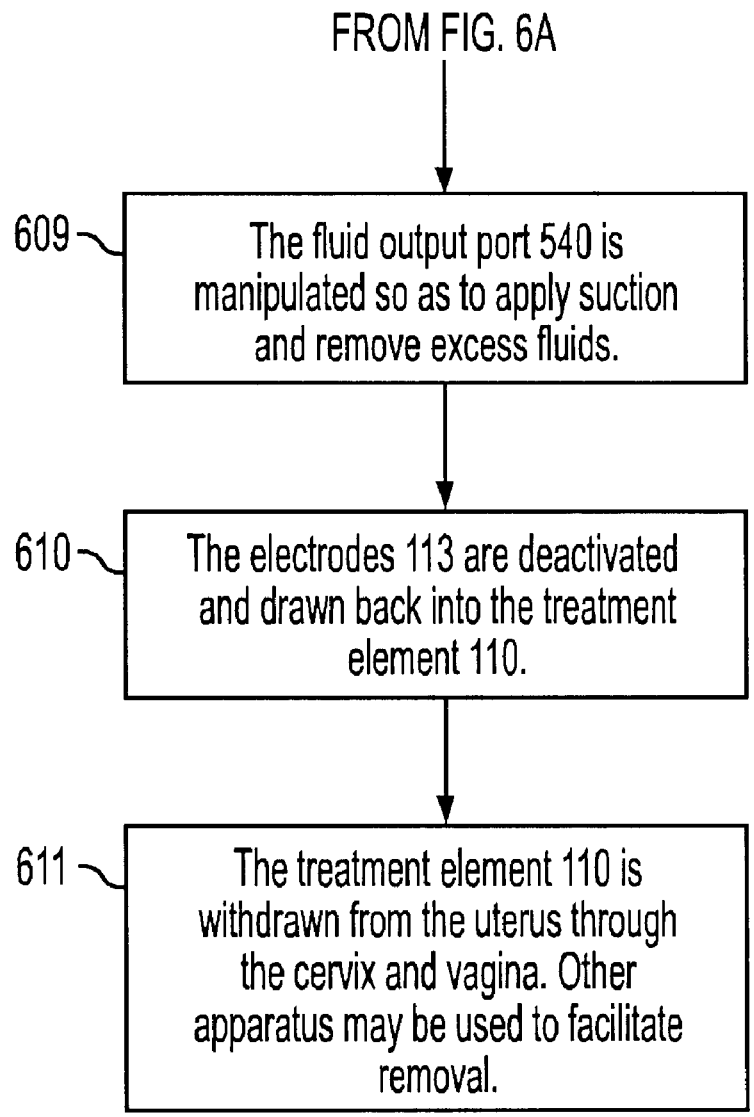

FIG. 6 is a process flow diagram showing method for using a first embodiment for intrauterine ablation.

A method 600 is performed to shrink discrete portions of the interior of a uterus, causing ablation of portions of the smooth muscle, so as to cause an improvement in menorrhagia and relate uterine conditions. Sterile technique is used throughout the procedure.

At a flow point 601, the patient has voided and is positioned on a treatment table, in an appropriate position such as horizontal, jackknife or lithotomy. The patient's external genitalia and surrounding anatomy are cleansed with an appropriate agent such as Betadine or benzalkonium chloride. The position of the patient and choice of cleansing agent are responsive to judgments by the physician.

In a step 602, the external genitalia may be pretreated with a topical anesthetic before insertion of the distal tip 111. Depending upon the circumstances, a muscle relaxant or short term tranquilizer may be indicated. The choice of topical anesthetic or other pharmacological agent are responsive to the judgments of the physician.

At a step 603, the electric connector 530 is coupled to a radio frequency generator or other source of therapeutic energy.

At a step 604, inflation or fluid infusion apparatus is coupled to the fluid input port 535. A pump or other apparatus may be coupled to the fluid output port 540. In this way, cooling fluids and pharmacological agents may be administered.

At a step 605, the distal tip 111 is lubricated. The distal tip 111 is introduced into the vagina, through the cervix and into the uterus. In a preferred embodiment, insertion may be facilitated by the use of a speculum, introducer tube and other apparatus. The choice of lubricant and additional apparatus is responsive to judgments by medical personnel.

At a step 606, the treatment element 110 is positioned within the uterus so as to be in optimal contact with the tissue to be treated.

In a step 607, the fluid input port 535 is manipulated so as to begin infusing a cooling fluid to the irrigation port 112. In a preferred embodiment, the cooling fluid may include sterile water, saline or glycerin. This cooling fluid lowers the relative temperature of the targeted tissues and prevents collateral thermal damage of the uterine walls and associated tissues. In alternative embodiments, other devices may be coupled to the fluid input port 535 to chill the cooling fluid or cause sonic cooling, gas expansion, magnetic cooling or others cooling methodologies. Other substances such lubricants, anesthetics, anti-spasmodics, anti-inflammatories, antiobiotics or other agents as deemed appropriate by the judgment of medical personal may also be administered via the fluid input port 535. The choice of cooling fluid or methodology or pharmaceutical substances is responsive to judgments by medical personnel.

In a step 608, the electrode control element 525 is manipulated so as to extend the electrodes 113 into the targeted uterine tissue. The electrodes 113 penetrate the mucosal (surface) tissue lining and enter more deeply into the underlying smooth muscle of the uterus. As the saline irrigation flows, radiofrequency energy is delivered through the electrodes 113, creating areas of ablative lesions within the interior of the uterus. During this step, the temperatures of the electrodes 113 are monitored. If necessary, the radiofrequency energy supply to any electrode 113 can be discontinued.

In a preferred embodiment, the position of the treatment element 110 can be altered so and the physician may repeat the treatment sequence so as to selectively ablate other areas in the interior of the uterus.

This treatment causes the affected area to shrink and be relatively strengthened, so as to relieve menorrhagia and other related uterine disorders. The tiny sites of treated muscle will ultimately resorb, remodel and shrink over the ensuing weeks.

In a step 609, the fluid output port 540 is manipulated so as to apply suction and remove excess fluids.

In a step 610, the electrodes 113 are deactivated and drawn back into the treatment element 110.

In a step 611, the treatment element 110 is withdrawn from the uterus through the cervix and vagina. Other apparatus may be used to facilitate removal.

Figure 7A:
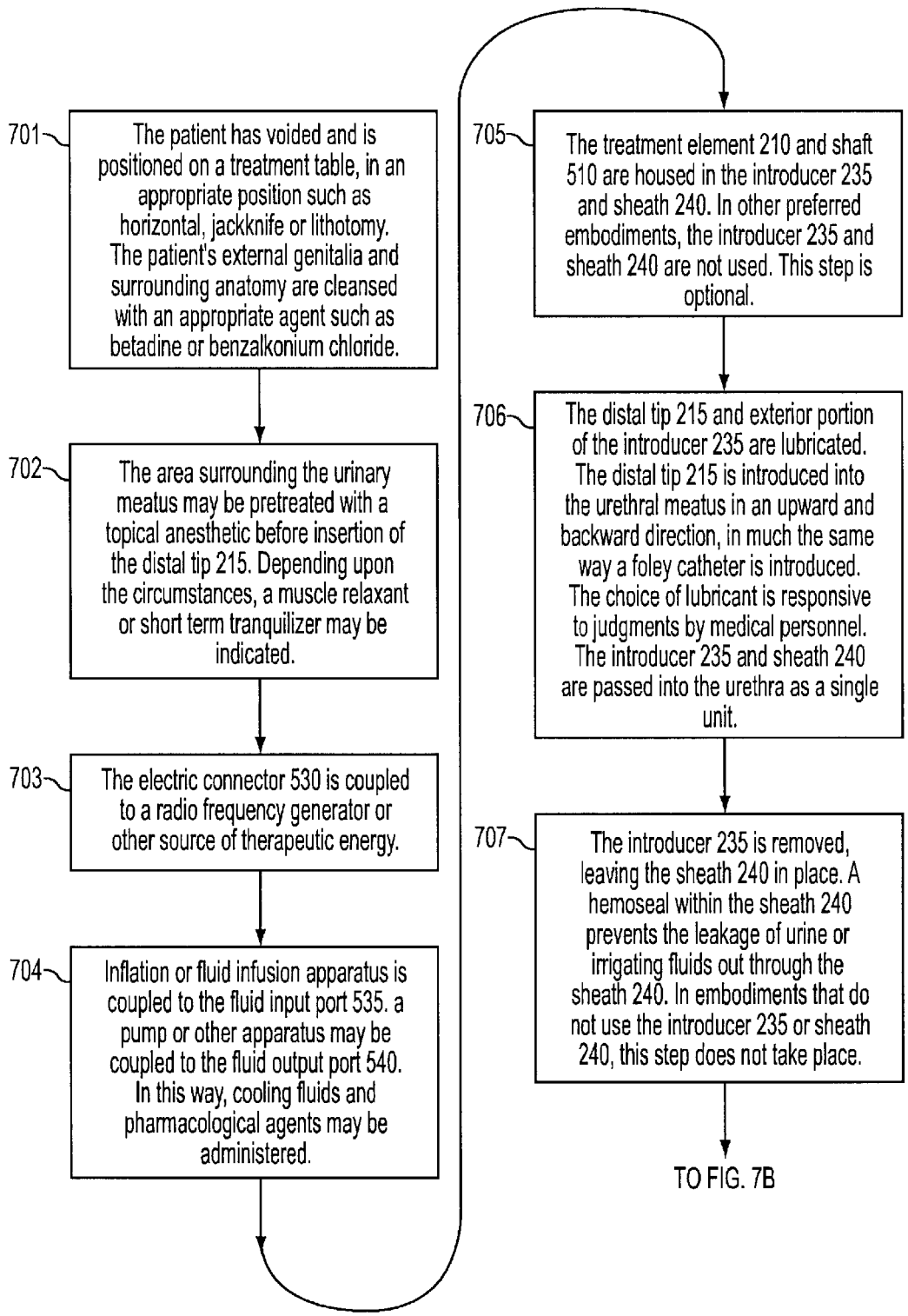
FIG. 7 is a process flow diagram showing a method for using a second embodiment for urethral remodeling.
Figure 7B:
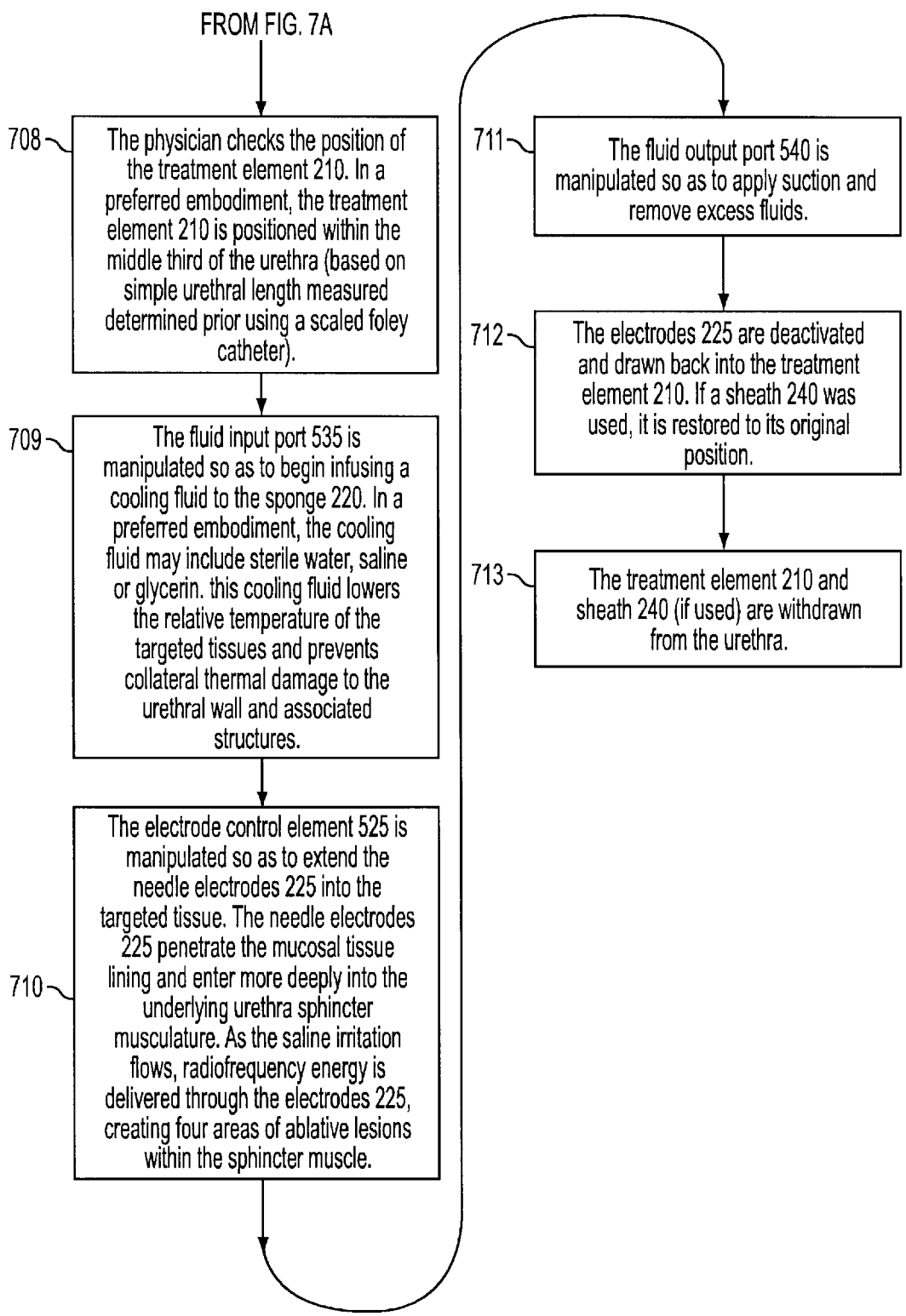

FIG. 7 is a process flow diagram showing a method for using a second embodiment for urethral remodeling.

A method 700 is performed to shrink the circular, external urethral sphincter muscle, so as to cause an improvement in its relative ability to retain urine. Sterile technique is used throughout the procedure.

At a flow point 701, the patient has voided and is positioned on a treatment table, in an appropriate position such as horizontal, jackknife or lithotomy. The patient's external genitalia and surrounding anatomy are cleansed with an appropriate agent such as Betadine or benzalkonium chloride. The position of the patient and the choice of cleansing agent are responsive to judgments of the physician.

At a step 702, the area surrounding the urinary meatus may be pretreated with a topical anesthetic before insertion of the distal tip 215. Depending upon the circumstances, a muscle relaxant or short term tranquilizer may be indicated. The choice of topical anesthetic and other drugs is responsive to judgments by the physician.

At a step 703, the electric connector 530 is coupled to a radio frequency generator or other source of therapeutic energy.

At a step 704, inflation or fluid infusion apparatus is coupled to the fluid input port 535. A pump or other apparatus may be coupled to the fluid output port 540. In this way, cooling fluids and pharmacological agents may be administered.

In a step 705, the treatment element 210 and shaft 510 are housed in the introducer 235 and sheath 240. In other preferred embodiments, the introducer 235 and sheath 240 are not used. This step is optional.

At a step 706, the distal tip 215 and exterior portion of the introducer 235 are lubricated. The distal tip 215 is introduced into the urethral meatus in an upward and backward direction, in much the same way a foley catheter is introduced. The choice of lubricant is responsive to judgments by medical personnel. The introducer 235 and sheath 240 are passed into the urethra as a single unit.

In other preferred embodiments, the introducer 235 and sheath 240 are not used. In these embodiments, the distal tip 215 is lubricated and introduced without the use of additional apparatus.

In a step 707, the introducer 235 is removed, leaving the sheath 240 in place. A hemoseal within the sheath 240 prevents the leakage of urine or irrigating fluids out through the sheath 240. In embodiments that do not use the introducer 235 or sheath 240, this step does not take place.

In a step 708, the physician checks the position of the treatment element 210. In a preferred embodiment, the treatment element 210 is positioned within the middle third of the urethra (based on simple urethral length measured determined prior using a scaled foley catheter).

In a step 709, the fluid input port 535 is manipulated so as to begin infusing a cooling fluid to the sponge 220. In a preferred embodiment, the cooling fluid may include sterile water, saline or glycerin. This cooling fluid lowers the relative temperature of the targeted tissues and prevents collateral thermal damage to the urethral wall and associated structures. In alternative embodiments, other devices may be coupled to the fluid input port 535 to chill the cooling fluid or cause sonic cooling, gas expansion, magnetic cooling or others cooling methodologies. Other substances such as lubricants, anesthetics, anti-spasmodics, anti-inflammatories, antibiotics or other agents as deemed appropriate by the judgment of medical personal may also be administered via the fluid input port 535. The choice of cooling fluid or methodology or pharmaceutical substances is responsive to judgments by medical personnel.

In a step 710, the electrode control element 525 is manipulated so as to extend the needle electrodes 225 into the targeted tissue. The needle electrodes 225 penetrate the mucosal (surface) tissue lining and enter more deeply into the underlying urethra sphincter musculature. As the saline irritation flows, radiofrequency energy is delivered through the electrodes 225, creating four areas of ablative lesions within the sphincter muscle. During this step, the temperatures of the electrodes 225 is monitored. If necessary, the radiofrequency energy supply to any electrode 225 can be discontinued.

In a preferred embodiment, the position of the treatment element 210 can be altered so and the physician may repeat the treatment sequence within the urethral sphincter so as to create more areas of ablation lesions within the muscle.

This treatment causes the affected area to shrink and be relatively strengthened, so as to better retain urine. The tiny sites of treated muscle will ultimately resorb, remodel and shrink over the ensuing weeks, resulting in circumferential tightening of the urethral sphincter muscle and a subsequent improvement in urinary continence.

In a step 711, the fluid output port 540 is manipulated so as to apply suction and remove excess fluids.

In a step 712, the electrodes 225 are deactivated and drawn back into the treatment element 210. If a sheath 240 was used, it is restored to its original position.

In a step 713, the treatment element 210 and sheath 240 (if used) are withdrawn from the urethra.

Figure 8A:
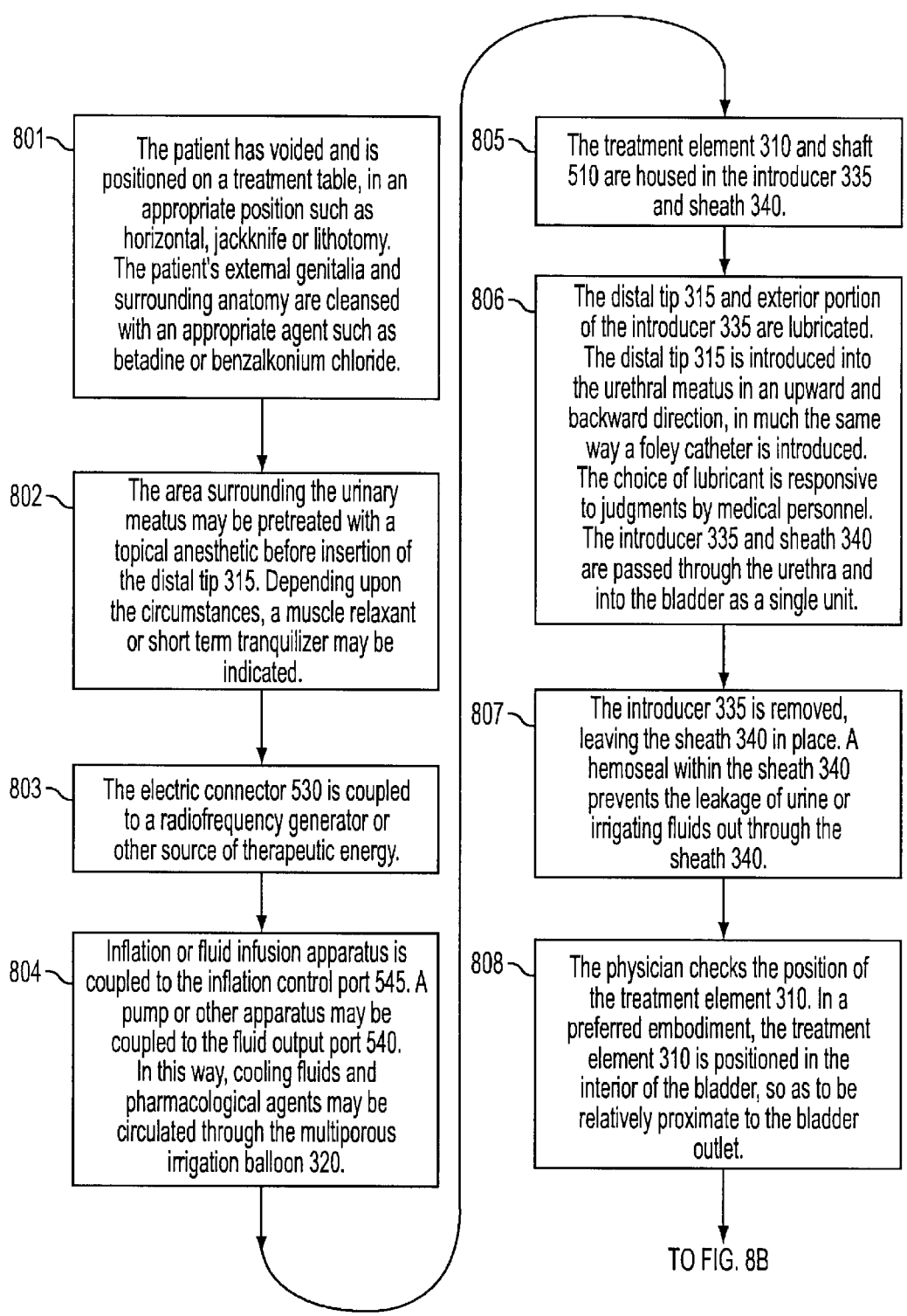
FIG. 8 is a process flow diagram showing a method for using a third embodiment for remodeling the bladder outlet.
Figure 8B:
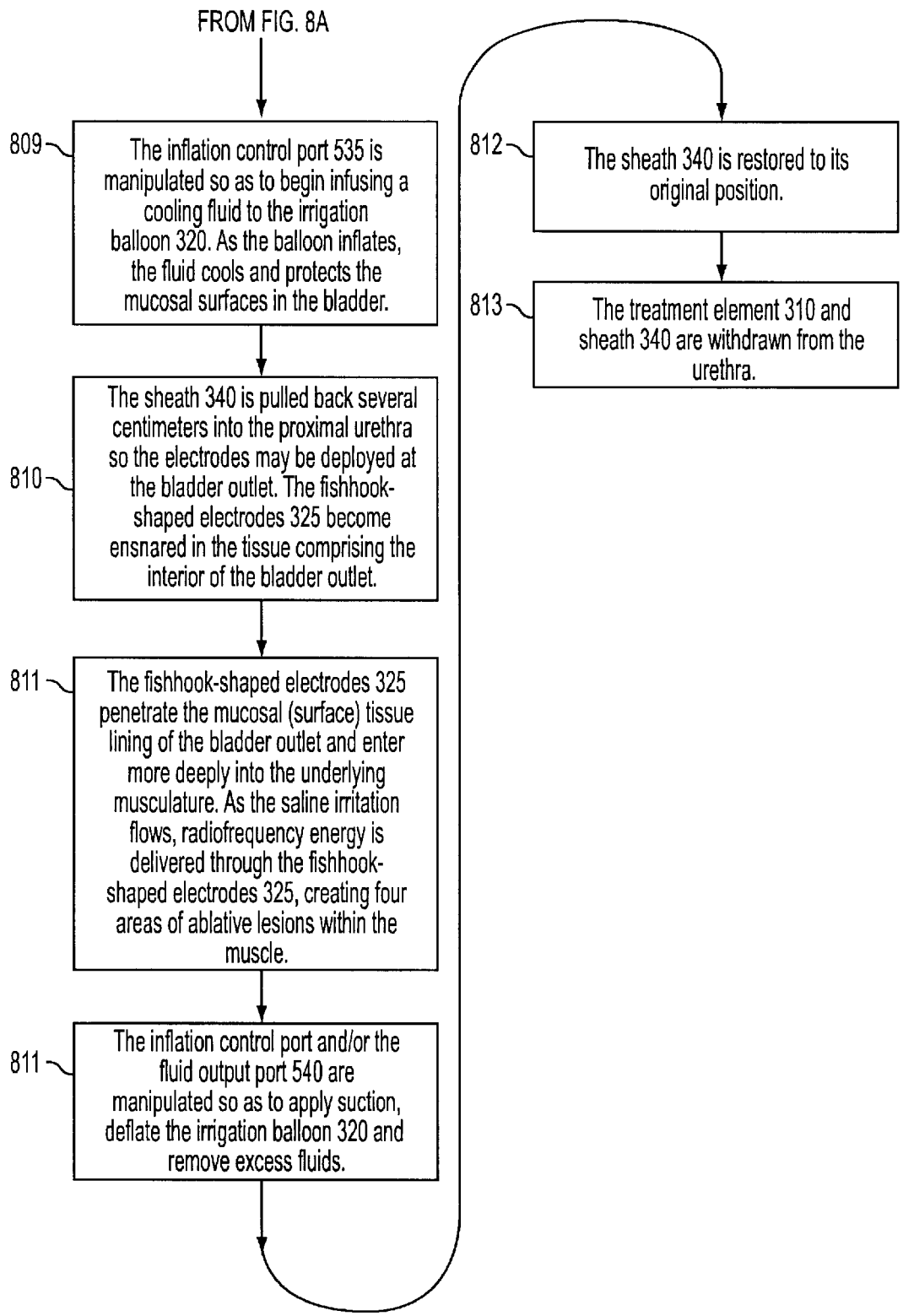

FIG. 8 is a process flow diagram showing a method for using a third embodiment for remodeling of the bladder outlet.

A method 800 is performed to reduce the size of the bladder outlet (the base of the bladder), resulting in decreased mobility during episodes of increased intra-abdominal pressure and increased resistance to the passage of urine into the proximal urethra during such episodes, thereby reducing urinary incontinence.

At a flow point 801, the patient has voided and is positioned on a treatment table, in an appropriate position such as horizontal, jackknife or lithotomy. The patient's external genitalia and surrounding anatomy are cleansed with an appropriate agent such as Betadine, or benzalkonium chloride. The positioning of the patient and choice of cleansing agent are responsive to the judgment of the physician.

At a step 802, the area surrounding the urinary meatus may be pretreated with a topical anesthetic before insertion of the distal tip 315. Depending upon the circumstances, a muscle relaxant or short term tranquilizer may be indicated. The choice of pharmaceutical agents to be used are responsive to judgments by the physician.

In a flow point 803, the electric connector 530 is coupled to a radiofrequency generator or other source of therapeutic energy.

In a flow point 804, inflation or fluid infusion apparatus is coupled to the inflation control port 545. A pump or other apparatus may be coupled to the fluid output port 540. In this way, cooling fluids and pharmacological agents may be circulated through the multiporous irrigation balloon 320.

In a step 805, the treatment element 310 and shaft 510 are housed in the introducer 335 and sheath 340.

At a step 806, the distal tip 315 and exterior portion of the introducer 335 are lubricated. The distal tip 315 is introduced into the urethral meatus in an upward and backward direction, in much the same way a foley catheter is introduced. The choice of lubricant is responsive to judgments by medical personnel. The introducer 335 and sheath 340 are passed through the urethra and into the bladder as a single unit.

In a step 807, the introducer 335 is removed, leaving the sheath 340 in place. A hemoseal within the sheath 340 prevents the leakage of urine or irrigating fluids out through the sheath 340.

In a step 808, the physician checks the position of the treatment element 310. In a preferred embodiment, the treatment element 310 is positioned in the interior of the bladder, so as to be relatively proximate to the bladder outlet. The depth of insertion is determined by prior measurements obtained using a scaled foley catheter.

In a step 809, the inflation control port 535 is manipulated so as to begin infusing a cooling fluid to the to the irrigation balloon 320. As the balloon inflates, the fluid cools and protects the mucosal surfaces in the bladder.

In a step 810, sheath 340 is pulled back several centimeters into the proximal urethra so that the electrodes may be deployed at the bladder outlet. In a preferred embodiment, the exposed U-shaped electrodes 325 become ensnared in the tissue comprising the interior of the bladder outlet.

In a step 811, the U-shaped electrodes 325 penetrate the mucosal (surface) tissue lining of the bladder outlet and enter more deeply into the underlying musculature. As the saline irritation flows, radiofrequency energy is delivered through the U-shaped electrodes 325, creating four areas of ablative lesions within the muscle. During this step, the temperatures of individual electrodes 325 are monitored. If necessary, the radiofrequency energy supply to any individual electrode 325 can be discontinued.

In a preferred embodiment, the position of the treatment element 310 can be altered so and the physician may repeat the treatment sequence within the bladder so as to create more areas of ablation lesions within the muscle.

In another preferred embodiment, the external mapping electrode network 321 may be engaged to identify nerves associated with the urge to urinate. Radiofrequency energy may be directed at these areas so as to ablate the identified nerves.

In another preferred embodiment, bulking agents, foreign bodies and other substances, such as organic microspheres, collagens, silicone, PVC and other organic breathable and unbreathable polymers are exuded from selected electrodes 325 into tissues comprising the bladder outlet. The type of microspheres and bulking substances and the locations where they are exuded are responsive to judgment by medical personnel. These substances can be used to strengthen these structures so as to prevent incontinence caused by stress.

These treatments cause the affected area to shrink and be relatively strengthened, so as to better retain urine. The tiny sites of treated muscle will ultimately resorb, remodel and shrink over the ensuing weeks, resulting in circumferential tightening of the urethral sphincter muscle and a subsequent improvement in urinary continence In a step 811, the inflation control port and/or the fluid output fluid output port 540 are manipulated so as to apply suction, deflate the irrigation balloon 320 and remove excess fluids.

In a step 812, the sheath 340 is restored to its original position.

In a step 813, the treatment element 310 and sheath 340 are withdrawn from the urethra.

Figure 9A:
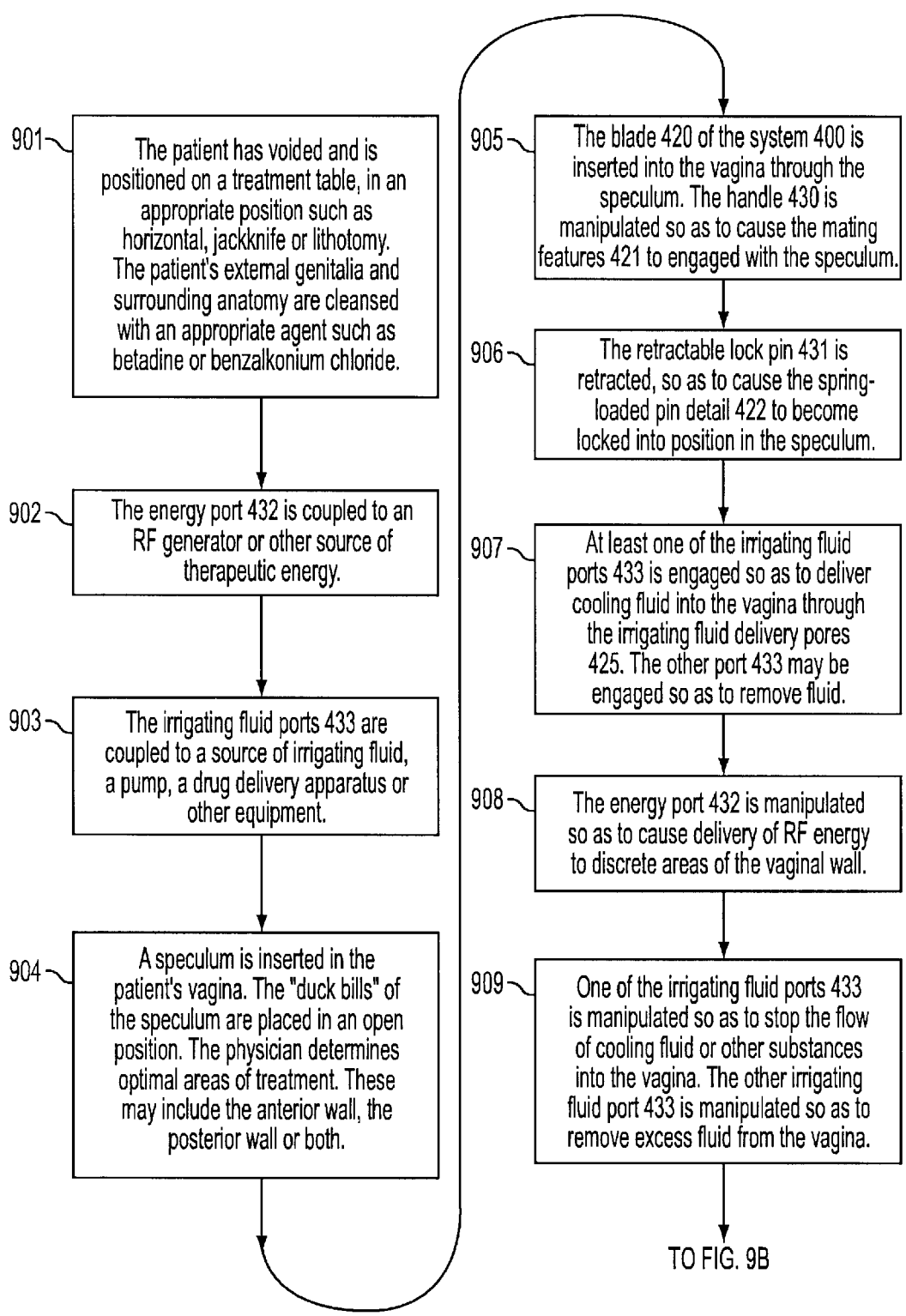
FIG. 9 is a process flow diagram showing a method for using a fourth embodiment for vaginal remodeling.

FIG. 9 is a process flow diagram showing a method for using a fourth embodiment for vaginal remodeling.

A method 900 is performed to create a series of lesions in either the anterior vaginal wall, the posterior vaginal wall or both. Remodeling of the anterior wall treats incontinence based on bladder outlet hypermobility by increasing support for the bladder outlet, as well as the proximal and midurethra. Remodeling both the anterior wall and posterior wall provide circumferential vaginal wall tightening, resulting physical and psychological improvement in the area of sexual function. The method 900 is performed using sterile technique.

At a flow point 901, the patient has voided and is positioned on a treatment table, in an appropriate position such as horizontal, jackknife or lithotomy. The patient's external genitalia and surrounding anatomy are cleansed with an appropriate agent such as Betadine, or benzalkonium chloride. The positioning of the patient and choice of cleansing agent are responsive to the judgment of the physician.

In a step 902, the energy port 432 is coupled to an RF generator or other source of therapeutic energy.

In a step 903, the irrigating fluid ports 433 are coupled to a source of irrigating fluid, a pump, a drug delivery apparatus or other equipment. The choice of fluid and apparatus is responsive to judgments on the part of the physician.

In a step 904, a speculum is inserted in the patient's vagina. The blades of the speculum are placed in an open position. The physician determines optimal areas of treatment. These may include the anterior wall, the posterior wall or both.

In a step 905, the blade 420 of the system 400 is inserted into the vagina through the speculum. The handle 430 is manipulated so as to cause the mating features 421 to engaged with the speculum.

In a step 906, the retractable lock pin 431 is retracted, so as to cause the spring-loaded pin detail 422 to become locked into position in the speculum.

In a step 907, at least one of the irrigating fluid ports 433 is engaged so as to delivery cooling fluid into the vagina through the irrigating fluid delivery pores 425. The other port 433 may be engaged so as to remove fluid.

In a step 908, the energy port 432 is manipulated so as to cause delivery of RF energy to discrete areas of the vaginal wall.

In alternative embodiments, other forms of energy may be delivered, such as microwave, laser, ELF (extremely low frequency) and other therapeutic energies.

In a preferred embodiment, the blade 420 may be disengaged and relocked into another position in the speculum, so as to delivry energy to another area of the vagina.

In a step 909, one of the irrigating fluid ports 433 is manipulated so as to stop the flow of cooling fluid or other substances into the vagina. The other irrigating fluid port 433 is manipulated so as to remove excess fluid from the vagina.

In a step 910, retractable lock pin 431 is manipulated so as to release the spring-loaded pin detail 422 from the speculum. The blade 420 is withdrawn from the vagina. The speculum is closed and removed.

Alternative Embodiments

Although preferred embodiments are disclosed herein, many variations are possible which remain within the concept, scope, and spirit of the invention, and these variations would become clear to those skilled in the art after perusal of this application.

What is claimed is:

1. An apparatus for treating female incontinence by remodeling tissue surrounding a patient's urethra, comprising:
   a plurality of electrodes adapted to deliver energy to urethral tissue;
   means for individually controlling each electrode of said plurality of electrodes; and
   means for delivering fluids in the vicinity of said plurality of electrodes, said means for delivering fluids comprising a sponge.

2. An apparatus as in claim 1, wherein said plurality of electrodes are needle shaped.

3. An apparatus as in claim 1, wherein said plurality of electrodes is disposed to deliver radio frequency energy.

4. An apparatus as in claim 1, wherein said plurality of electrodes are disposed to deliver microwave energy.

5. An apparatus as in claim 1, wherein said plurality of electrodes are disposed to deliver laser energy.

6. An apparatus as in claim 1, wherein said plurality of electrodes are disposed to deliver extremely low frequency energy.

7. An apparatus as in claim 1, wherein said plurality of electrodes are two to four in number.

8. An apparatus as in claim 1, wherein said plurality of electrodes are engaged to penetrate the muscosal tissue so as to become embedded in the muscle wall.

9. Apparatus as in claim 1, wherein each electrode of said plurality of electrodes also includes a thermocouple.

10. Apparatus as in claim 1, wherein said means for controlling includes a means for adjusting said electrodes so that said electrodes protrude at different distances so as to be deployed at different depths in a targeted tissue.

11. Apparatus as in claim 1, wherein said means for controlling includes a means for adjusting the temperature of each electrode.

12. Apparatus as in claim 1, wherein said electrodes are situated so as to emerge at an angle from said means for delivering fluids with the tip of said electrodes splayed out in a distal orientation, said angle ranging from ten to one hundred and seventy degrees.

13. An apparatus as in claim 1, wherein said electrodes are situated so as to emerge at an angle from said means for delivering fluids with the tip of said electrodes splayed out in a distal orientation, said angle ranging from ten to one hundred and seventy degrees and wherein said electrodes are longitudinally staggered along the length of said means for delivering.

14. Apparatus as in claim 1, wherein said means for delivering is disposed to deliver cooling liquids to a portion of the urethral muscosa.

15. Apparatus as in claim 1, wherein said means for delivering is disposed to deliver pharmaceutical agents to a portion of the urethral mucosa.

16. A method for treating female urinary incontinence comprising:
   inserting a treatment element including a plurality of electrodes and a sponge into a urethra;

deploying the plurality of electrodes so as to penetrate the urethral mucosa and penetrate into the underlying muscle; and delivering energy so as to create a pattern of lesions within the urethral sphincter that remodels the sphincter.

17. A method as in claim 16, including a step for:

infusing said sponge with cooling fluids.

18. A method as in claim 16, wherein the step for inserting is performed using an introducer and sheath.

19. A method as in claim 16, wherein said step for inserting includes inserting the treatment element into the middle third of a urethra.

20. A method as in claim 16, wherein said step for infusing the sponge also include the step of infusing said sponge with pharmacological agents and drugs.

21. A method as in claim 16, wherein said step for delivering energy includes delivery of RF energy, microwave energy, laser energy or other extremely low frequency energy.

22. A method as in claim 16, includes steps for removing said treatment element from the urethra.

23. Apparatus for treating female incontinence by remodeling the urethral wall, the apparatus comprising:

an elongated shaft having a distal region;

a plurality of electrodes disposed in the distal region, the plurality of electrodes movable from a retracted position disposed within the elongated shaft to a deployed position extending from the distal region; and a sponge disposed in the distal region to deliver fluids to the urethral wall in the vicinity of the plurality of electrodes.

24. The apparatus of claim 23, wherein each one of the plurality of electrodes comprises a curved needle.

25. The apparatus of claim 23, wherein the plurality of electrodes includes between two and four electrodes.

26. The apparatus of claim 23, wherein the plurality of electrodes are configured to penetrate the muscosal tissue in the deployed position.

27. The apparatus of claim 23, wherein each electrode of the plurality of electrodes further comprises a thermocouple.

28. The apparatus of claim 23 further comprising means for individually controlling each one of the plurality of electrodes.

29. The apparatus of claim 28, wherein the means for controlling further comprises means for adjusting the extent to which each one of the electrodes extend from the elongated shaft in the deployed position.

30. The apparatus of claim 23, wherein the means for controlling further comprises means for adjusting a temperature of each one of the plurality of electrodes.

31. The apparatus of claim 23, wherein the plurality of electrodes extend through the sponge in the deployed state.

32. The apparatus of claim 23, wherein the plurality of electrodes are longitudinally staggered along the distal region.

33. The apparatus of claim 23, wherein the sponge is adapted to deliver a cooling liquid to a portion of the urethral muscosa.

34. The apparatus of claim 23, wherein the sponge is adapted to deliver pharmaceutical agents to a portion of the urethral muscosa.

35. A method for treating female incontinence comprising:

providing a treatment device comprising a shaft having a distal region, a plurality of electrodes disposed in the distal region, and a sponge for delivering fluids in the vicinity of the plurality of electrodes;

inserting the distal region of the treatment device into a patient's urethra;

moving the plurality of electrodes to a deployed position, wherein the plurality of electrodes penetrate the urethral mucosa and extend into tissue surrounding the urethra;

infusing a cooling fluid to the urethral mucosa through the sponge; and delivering energy to the plurality of electrodes to create a pattern of lesions in the tissue surrounding the urethra.

36. The method of claim 35 wherein inserting the distal region comprises inserting the distal region using an introducer sheath.

37. The method of claim 36 wherein inserting the distal region comprises inserting the distal region into a middle third of the urethra.

38. The method of claim 36 further comprising infusing a pharmacological agent or drug to the urethral mucosa through the sponge.

39. The method of claim 36 wherein delivering energy to the plurality of electrodes comprises delivering RF energy.

40. The method of claim 36 wherein each one of the plurality of electrodes further comprises a thermocouple, the method further comprising monitoring a temperature of each one of the plurality of electrodes.

41. The method of claim 40 further comprising, during delivery of energy to the plurality of electrodes, adjusting the temperature of each one of the plurality of electrodes.

42. The method of claim 36 wherein moving the plurality of electrodes to the deployed position further comprises individually adjusting an extent to which each one of the plurality of electrodes laterally extends from the shaft.

* * * * *

UNITED STATES PATENT AND TRADEMARK OFFICE
CERTIFICATE OF CORRECTION

PATENT NO. : 6,463,331 B1
DATED : October 8, 2002
INVENTOR(S) : Edwards

It is certified that error appears in the above-identified patent and that said Letters Patent is hereby corrected as shown below:

Drawings,
Figure 6A, Box 604, Sheet 6 of 13, replace "535.a" with -- 535.A --
Figure 6A, Box 605, Sheet 6 of 13, replace "lubricated. the" with -- lubricated. The --
Figure 7A, Box 704, Sheet 8 of 13, replace "535.a" with -- 535.A --
Figure 7B, Box 709, Sheet 9 of 13, replace "glycerin. this" with -- glycerin. This --
Figure 8B, Box 811, Sheet 11 of 13, replace "irritation" with -- irrigation --

Column 2,
Line 64, replace "muscosa" with -- mucosa --

Column 4,
Line 22, replace "RF 2 energy" with -- RF energy --
Line 44, replace "(not shown) Depending" with -- (not shown). Depending --
Line 64, replace "225 are take" with -- 225 take --

Column 5,
Line 13, replace "thermo-couple" with -- thermocouple --

Column 6,
Line 35, replace "two-four" with -- two - four --
Line 61, replace "indroducer" with -- introducer --

Column 7,
Line 54, replace "43 1" with -- 431 --
Line 64, replace "a t" with -- at --

Column 8,
Line 32, replace "includes" with -- included --

Column 9,
Line 7, replace "relate" with -- related --
Lines 63-64, replace "radiof-requency" with -- radio-frequency --

Column 11,
Line 10, replace "others" with -- other --
Line 10, add -- as -- after "such"
Line 22, replace "irritation" with -- irrigation --

UNITED STATES PATENT AND TRADEMARK OFFICE
CERTIFICATE OF CORRECTION

PATENT NO. : 6,463,331 B1
DATED : October 8, 2002
INVENTOR(S) : Edwards

It is certified that error appears in the above-identified patent and that said Letters Patent is hereby corrected as shown below:

Column 13,
Line 4, replace "continence" with -- continence. --
Lines 5-6, delete second instance of "fluid output"
Lines 20-21, insert -- in -- between "resulting" and "physical"
Line 51, replace "delivery" with -- deliver --
Line 62, replace "delivry" with -- deliver --

Column 14,
Line 35, replace "muscosal" with -- mucosal --
Line 60, replace "muscoca" with -- mucosa --

Column 15,
Line 15, replace "include" with -- includes --
Line 21, replace "includes" with -- including --
Line 39, replace "muscosal" with -- mucosal --
Line 48, replace "extend" with -- extends --

Column 16,
Line 2, replace "extend" with -- extends --
Lines 8 and 11, replace "muscosa" with -- mucosa --
Line 22, replace "penetrate" with -- penetrates --
Line 23, replace "extend" with -- extends --

Signed and Sealed this

Twenty-ninth Day of June, 2004

JON W. DUDAS
*Acting Director of the United States Patent and Trademark Office*